(12) United States Patent
O'Lenick, Jr.

(10) Patent No.: US 6,566,474 B1
(45) Date of Patent: May 20, 2003

(54) PHOSPHATE POLYMERS

(75) Inventor: Anthony J. O'Lenick, Jr., Dacula, GA (US)

(73) Assignee: Colonial Chemical Inc, So. Pittsburgh, TN (US)

(*) Notice: Subject to any disclaimer, the term of this patent is extended or adjusted under 35 U.S.C. 154(b) by 0 days.

(21) Appl. No.: 10/103,090

(22) Filed: Mar. 22, 2002

Related U.S. Application Data

(63) Continuation-in-part of application No. 09/596,705, filed on Jun. 19, 2000.
(51) Int. Cl.$^7$ ............................................. C08F 130/02
(52) U.S. Cl. ...................... 526/277; 526/264; 526/274; 526/287; 526/288; 526/303.1; 526/317.1
(58) Field of Search ................................. 526/264, 274, 526/277, 287, 288, 303.1, 317.1

(56) References Cited

U.S. PATENT DOCUMENTS

| | | | | |
|---|---|---|---|---|
| 4,479,893 A | * | 10/1984 | Hirota et al. | ................ 252/542 |
| 5,162,472 A | | 11/1992 | O'Lenick | |
| 6,117,915 A | * | 9/2000 | Pereira et al. | ................. 516/57 |

FOREIGN PATENT DOCUMENTS

| | | | |
|---|---|---|---|
| EP | 0 985 401 A2 | * | 3/2000 |
| WO | 96/14145 | * | 5/1996 |

* cited by examiner

*Primary Examiner*—Helen L. Pezzuto

(57) ABSTRACT

The present invention deals with the composition, and application of novel phosphate polymers. The polymeric compounds are useful as emulsifying agents, softening, anti-tangle, and conditioning agents for use in personal care applications due to their outstanding mildness.

6 Claims, No Drawings

PHOSPHATE POLYMERS

RELATED APPLICATION

This application is a continuation in part of Ser. No. 09/596,705 filed Jun. 19, 2000, allowed.

BACKGROUND OF THE INVENTION

1. Field of the Invention

The present invention deals with the composition, and application of novel phosphate polymers. The compounds are useful as in personal care applications due to their outstanding emulsification properties, and because they are polymeric do not penetrate skin, making them non-irritating. The properties of these novel compounds that makes them well suited for these applications is the fact that they are substantive to fibers, hair and skin and also very mild to the skin and eyes and provide protection from environmental factors like acid rain and other pollutions which come in contact with hair and skin. The use of the compounds results in several additional desirable properties heretofore unattainable. This includes overcoming the problem of eye and skin irritation using traditional cationic conditioning agents.

2. Arts and Practices

The prior practices for providing softening, anti-tangle, and conditioning properties for use in personal care, textile and related applications has been incorporation of quaternary compounds. These materials have been used for many years despite some significant drawbacks including irritation, negative impact on the aquatic environment, build up and yellowing of the substrate upon which they are applied.

U.S. Pat. No. 5,162,472 to O'Lenick discloses free radical polymers which incorporate silicone into the backbone. While these materials have desirable properties, they do not have an ionizable phosphate group in the molecule.

The references cited herein are incorporated by reference to the extent applicable. Ratios and percentages are by weight and temperatures are Celsius unless otherwise stated.

THE INVENTION

Object of the Invention

It is the object of the current invention to provide a novel series of anionic free radical polymers. The polymers are made by homo-polymerization of the novel phosphate monomer or by polymerization with a variety of other vinyl containing free radical reactive monomers. The formation of a high molecular weight polymer results in less penetration of the skin by the compounds of the present invention and a very effective conditioner that remains on the surface of the hair or skin where the conditioning agent is most effective.

It is another object of the current invention to provide a novel allyl alkoxy phosphates used as an intermediate in the preparation of the compounds of the present invention.

Still another objective of the current invention to provide personal care compositions which contain an effective conditioning amount of the compounds of the current invention. That effective conditioning concentration will vary from 0.1 to 20% of the composition. The compounds of the present invention have outstanding conditioning properties when applied to hair and skin.

SUMMARY OF THE INVENTION

The present invention is directed to free radical polymers which contain a phosphate group as one of the functional groups polymerized. The compounds of the invention are prepared by the free radical polymerization of a novel allyl phosphate monomer.

The phosphate functional allyl monomer is polymerized and subsequently used as the emulsification and conditioning agents for hair and skin.

The allyl alkoxy phosphate used to make the compounds of the present invention conform to the following structure:

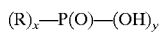

wherein;

R is $CH_2=CH-CH_2-O-(CH_2CH_2O)_s-(CH_2CH(CH_3)O)_t-(CH_2CH_2O)_u$;

s, t and u are integers each independently ranging from 0 to 20;

x and y are each independently 1 or 2, with the proviso that x+y=3.

The compounds are made by the reaction of allyl alcohol alkoxylates, which are commercially available with a phosphating agent selected from polyphosphoric acid or $P_2O_5$.

When polyhosphohric acid is used the products are primarily compounds in which x is 1 and y is 2.

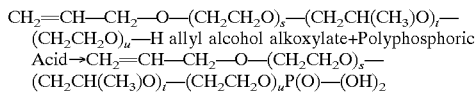

When $P_2O_5$ is used the products are primarily compounds in which x is 2 and y is 1.

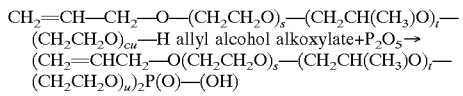

These allyl alkoxy phosphates are key materials to synthesis the polymers of the present invention. The polymers conform to the following structure;

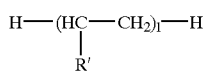

wherein;

R' is $-CH_2-O-(CH_2CH_2O)_s-(CH_2CH(CH_3)O)_t-(CH_2CH_2O)_u-P(O)-(OH)_2$ s, t and u are integers each independently ranging from 0 to 20;

l is an integer from 10 to 2,000.

The compounds of the current invention are prepared by the free radical reaction of the allyl alkoxy phosphate containing monomer.

The compounds of the current invention conform to the following generic structure;

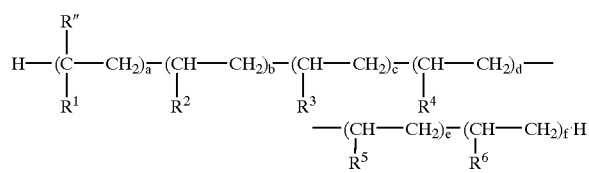

wherein;

R' is selected from the group consisting of CH3 and H;

a is an integer from 1 to 100;

b, c, d, e, and f are integers ranging from 0 to 100;
R$^1$ is —CH$_2$—O—(CH$_2$CH$_2$O)$_s$—(CH$_2$CH(CH$_3$)O)$_t$—(CH$_2$CH$_2$O)$_u$P(O)—(OH)$_2$
s, t and u are independently integers ranging from 0 to 20;
R$^2$ is —C(O)—$\overline{\text{M}}^+$
M is selected from H, Na, K, Li, and NH 4;
R$^3$ is

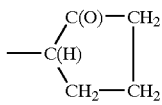

R$^4$ is

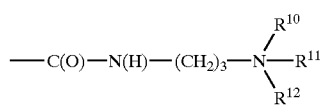

R$_{10}$, R$^{11}$ and R$^{12}$ are selected from H, methyl and ethyl;
R$^5$ is —C(O)—NH$_2$
R$^6$ is —C(0)—N(H)—(CH$_2$)$_q$—SO$_3^-$M$^+$
q is an integer ranging from 1 to 5.

The compounds of the current invention are prepared by the free radical reaction of a meadowfoam ester containing monomer and other monomers selected from the following;
R$^1$ is derived from the monomer conforming to the following structure;

CH$_2$=CH—CH$_2$—O—(CH$_2$CH$_2$O)$_s$—(CH$_2$CH(CH$_3$)O)$_t$—(CH$_2$CH$_2$O)$_u$P(O)—(OH)$_2$ s, t and u are independently integers ranging from 0 to 20;
R$^2$ is derived from the following monomer CH$_2$=CH—C(O)—O$^-$M$^+$
Acrylic acid and methacrylic acid is available from Dow.
R$^3$ is derived from the following monomer;

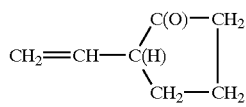

Vinyl pyrrolidone is available commercially from BASF.
R$^4$ is derived from the following monomer;

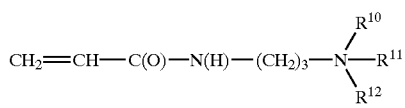

R$^{10}$, R$^{11}$ and R$^{12}$ are selected from H, methyl and ethyl;
These monomers are available from CPS Corporation.
R$^5$ is derived from the following monomer CH$_2$=CH—C(O)—NH$_2$
Acrylamide is available from Dow Chemical.
R$^6$ is derived from the following monomer;

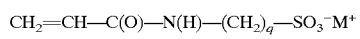

These materials are available from Lubrizol Inc.
These materials are reacted in a solvent, typically water under the influence of a free radical catalyst. Free radical polymerization is well known to those skilled in the art.

Preferred Embodiments

In a preferred embodiment b, c, d, e, and f are all zero and a and b are independently integers ranging from 1 to 100.

In a preferred embodiment b, d, e and f are all zero and a and c are independently integers ranging from 1 to 100.

In a preferred embodiment b, c, e and f are all zero and a and d are independently integers ranging from 1 to 100.

In a preferred embodiment b, c, d and f are all zero and a and e are independently integers ranging from 1 to 100.

In a preferred embodiment b, c, d and e are all zero and a and f are independently integers ranging from 1 to 100.

In a preferred embodiment x and y are 0.

EXAMPLES

Raw Materials
Allyl Alcohol Alkoxylates
These compounds conform to the following structure:

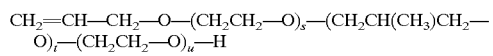

| Example Number | s | t | u |
|---|---|---|---|
| 1 | 0 | 0 | 0 |
| 2 | 0 | 1 | 0 |
| 3 | 4 | 0 | 0 |
| 4 | 7 | 0 | 0 |
| 5 | 10 | 0 | 0 |
| 6 | 20 | 0 | 0 |
| 7 | 4 | 7 | 10 |
| 8 | 7 | 4 | 20 |
| 9 | 10 | 20 | 4 |
| 10 | 20 | 10 | 7 |
| 11 | 20 | 20 | 20 |
| 12 | 7 | 7 | 7 |

These materials are items of commerce available commercially from Siltech Corporation Toronto Ontario Canada, and Pelron Corporation Chicago Ill.

Phosphation

Phosphating Agents
Polyphosphoric Acid (PPA) is 115% phosphoric acid. When used as a phosphating agent in gives more mono ester than the phosphorus pentoxide.

Phosphorus pentoxide is P$_2$O$_5$. It is more aggressive in phosphation and results in more diester.

The phosphates of this invention can be prepared by reacting the hydroxyl group with a suitable phosphating agent. Preferred phosphating reagents are polyphosphoric acid and phosphorus pentoxide.

General Procedure

The specified amount of allyl alkoxy compound example 1–12) is added to a suitable reaction vessel. The specified amount of either polyphosphoric acid or phosphorus pentoxide is charged to under good agitation over a 2 hr. period. The exothermic reaction raises the temperature of the mixture to about 70 C. After 1 hour slowly raise the temperature to 100 C. and hold 2–4 hours.

| Example | Allyl Example | Alkoxylate Grams | Polyphosphoric Acid Grams |
|---------|---------------|------------------|---------------------------|
| 13 | 1 | 57.0 | 98.0 |
| 14 | 2 | 116.0 | 98.0 |
| 15 | 3 | 233.0 | 98.0 |
| 16 | 4 | 365.0 | 98.0 |
| 17 | 5 | 497.0 | 98.0 |
| 18 | 6 | 937.0 | 98.0 |
| 19 | 7 | 1086.0 | 98.0 |
| 20 | 8 | 1481.0 | 98.0 |
| 21 | 9 | 1853.0 | 98.0 |
| 22 | 10 | 1835.0 | 98.0 |
| 23 | 11 | 2977.0 | 98.0 |
| 24 | 12 | 1499.0 | 98.0 |
| 25 | 1 | 57.0 | 47.6 |
| 26 | 3 | 233.0 | 47.6 |
| 27 | 5 | 497.0 | 47.6 |
| 28 | 7 | 1086.0 | 47.6 |
| 29 | 8 | 1481.0 | 47.6 |
| 30 | 9 | 1853.0 | 47.6 |
| 31 | 10 | 1835.0 | 47.6 |
| 32 | 11 | 2997.0 | 47.6 |

Preparation of Phosphate Homo-polymers

Examples 33–52
General Polymerization Procedure

The polymerization of the allyl phosphate compound is achieved by utilizing free radical catalyst in a low oxygen containing solvent, most commonly water. The water is deionized and sparged with nitrogen to remove dissolved oxygen contained therein immediately prior to use. Then, the specified amount of the treated de-ionized water is added to a suitable glass vessel. Most commonly, 50 to 80% of the total weight of the batch is water. The specified amount of the specified monomers are then added under agitation. Nitrogen is continuously sparged and the temperature is raised to about 50 C. Once the temperature has reached 50 and the nitrogen has been bubbled through the reaction mass for thirty minutes, a free radical initiator is added. Many peracids, like t-butyl-perbenzoate, t-butyl-hydroperoxide and inorganic free radical initiators like stannic chloride can be used. The preferred initiator is azobisisobutyl-nitrile. The reaction is exothermic and cooling is used to keep the temperature below 90 C. The molecular weight is monitored by viscosity and both increase as the reaction continues.

Homopolymers

Example 33

To the 5,000 grams of deionized water, which has just been sparged with nitrogen for 30 minutes, is added the specified amount 5,000 grams of the specified allyl phosphate monomer Ex #13 under good agitation and nitrogen sparge. The temperature is raised to about 50 C. Once the temperature has reached 50 and the nitrogen has been bubbled through the reaction mass for thirty minutes, 0.05% by weight of batch of azobisisobutylnitrile. The catalyst may be optimally added in smaller increments of one quarter of the total needed waiting 30 minutes between additions. The viscosity will raise as the polymerization occurs. The temperature raises to about 90 C. and is cooled with cooling water as needed to prevent the temperature from reaching 90 C. The molecular weight is controlled by viscosity. When the desired viscosity is achieved, air is bubbled through the vessel to quench the polymer. The desired polymer is used as prepared.

Examples 33–52

Example 33 is repeated only substituting the allyl phosphate monomer for example 13 used in example 49.

| Example | Allyl Phosphate Example |
|---------|------------------------|
| 33 | 13 |
| 34 | 14 |
| 35 | 15 |
| 36 | 16 |
| 37 | 17 |
| 38 | 18 |
| 39 | 19 |
| 40 | 20 |
| 41 | 21 |
| 42 | 22 |
| 43 | 23 |
| 44 | 24 |
| 45 | 25 |
| 46 | 26 |
| 47 | 27 |
| 48 | 28 |
| 49 | 29 |
| 50 | 30 |
| 51 | 31 |
| 52 | 32 |

Preparation of Phosphate Hetero-polymers

The vinyl containing compounds that were homo-polymerized in example 33–52 can be polymerized with other vinyl containing, free radical reactive monomers. These so-called heteropolymers have added functionality and provide unique properties.

Class 1 Vinyl Phosphate Compounds
Examples 13–32
Class 2 Vinyl Amino Compounds
Examples 53–57

$$CH_2{=}CH{-}C(O){-}N(H){-}(CH2)3{-}N{\diagup}^{R^{10}}_{\diagdown R^{12}}R^{11}$$

| Example | $R^{10}$ | $R^{11}$ | $R^{12}$ |
|---------|----------|----------|----------|
| 53 | Methyl | Methyl | Hydrogen |
| 54 | Methyl | Methyl | Methyl |
| 55 | Ethyl | Methyl | Hydrogen |
| 56 | Ethyl | Methyl | Methyl |
| 57 | Ethyl | Ethyl | Methyl |

Class 3 Vinyl Anionic Materials
Examples 58–61

$$CH_2{=}CH{-}C(O){-}N(H){-}(CH2)q\text{-}SO_3^- \; M^+$$

| Example | q | M |
|---------|---|---|
| 58 | 3 | H |
| 59 | 4 | H |
| 60 | 3 | Na |
| 61 | 3 | K |

Class 4 Vinyl Carboxylic Compounds
Example 62  Acrylic Acid  $CH_2{=}CH{-}C(O){-}OH$
Class 5 Vinyl Lactones
Example 63

Vinyl pyrrolidone $$CH_2{=}CH{-}C(H){\diagup}^{C(O){-}CH2}_{\diagdown CH2{-}CH2}$$

Class 6 Vinyl Amides
Example 64
Acrylamide  $CH_2{=}CH{-}C(O){-}NH_2$

Preparation of Hetero-polymers

Examples 65–93
General Polymerization Procedure

The polymerization of the vinyl containing meadowfoam esters is achieved by utilizing free radical catalyst in a low oxygen containing solvent, most commonly water. The water is deionized and sparged with nitrogen to remove dissolved oxygen contained therein immediately prior to use. Then, the specified amount of the treated de-ionized water is added to a suitable glass vessel. Most commonly, 50 to 80% of the total weight of the batch is water. The specified amount of the specified monomers are then added under agitation. Nitrogen is continuously sparged and the temperature is raised to about 50 C. Once the temperature has reached 50 and the nitrogen has been bubbled through the reaction mass for thirty minutes, a free radical initiator is added. Many peracids, like t-butyl-perbenzoate, t-butyl-hydroperoxide and inorganic free radical initiators like stannic chloride can be used. The preferred initiator is azobisisobutyl-nitrile. The reaction is exothermic and cooling is used to keep the temperature below 90 C. The molecular weight is monitored by viscosity and both increase as the reaction continues.

Example 65

To the specified number of grams (5,000 Gm.) of deionized water, which has just been spargred with nitrogen for 30 minutes, is added the specified amount (4,200 grams) of Class 1 monomer (Ex #13). Next add the specified amount (0 grams) of Class 2 monomer (Ex #53) followed by the specified amount (0 grams) of Class 3 monomer (Ex #58) followed by the specified amount (0 grams) of Class 4 monomer (Ex #64) followed by the specified amount (0 grams) of Class 5 monomer (Ex #63) followed by the specified amount (0 grams) of Class 6 monomer (Ex #64), under good agitation and nitrogen sparge. The temperature is raised to about 50 C. Once the temperature has reached 50 and the nitrogen has been bubbled through the reaction mass for thirty minutes, the specified amount of the specified catalyst (azobisisobutylnitrile) is added. The catalyst may be optimally added in smaller increments of one quarter of the total needed waiting 30 minutes between additions. The viscosity will raise as the polymerization occurs. The temperature raises to about 90 C. and is cooled with cooling water as needed to prevent the temperature from reaching 90 C. The desired polymer is used as prepared.

Examples 66–93

The above procedure is repeated only substituting the specified amount and type of monomer, catalyst and water specified.

|         | Example 66 | Example 67 | Example 68 | Example 69 |
|---------|------------|------------|------------|------------|
| Class 1 | Ex # 14    | Ex # 15    | Ex # 16    | Ex # 17    |
|         | 4,200 Gm.  | 3,860 Gm.  | 12,747 Gm. | 1,714 Gm.  |
| Class 2 | Ex # 53    | Ex # 54    | Ex # 55    | Ex # 56    |
|         | 157.0 Gm.  | 171.0 Gm.  | 185.0 Gm.  | 216.0 Gm.  |
| Class 3 | Ex # 58    | Ex # 59    | Ex # 60    | Ex # 61    |
|         | 193.0 Gm.  | 207.0 Gm.  | 215.0 Gm.  | 231.0 Gm.  |
| Class 4 | Ex # 62    | Ex # 62    | Ex # 62    | Ex #62     |
|         | 72.0 Gm.   | 0 Gm.      | 0 Gm.      | 0 Gm.      |
| Class 5 | Ex # 63    | Ex # 63    | Ex # 63    | Ex # 63    |
|         | 110.0 Gm.  | 1,100 Gm.  | 110.0 Gm.  | 0 Gm.      |
| Class 6 | Ex # 64    | Ex # 64    | Ex # 64    | Ex # 64    |
|         | 158.0 Gm.  | 1,580 Gm.  | 0 Gm.      | 0 Gm.      |
| Water   | 5,000 Gm.  | 10,000 Gm. | 20,000 Gm. | 5,000 Gms  |

Catalyst These examples used 0.05% by weight of batch of azobisisobutylnitrile

|         | Example 70 | Example 71 | Example 72 | Example 73 |
|---------|------------|------------|------------|------------|
| Class 1 | Ex # 18    | Ex # 19    | Ex # 20    | Ex # 21    |
|         | 13.5 Gm.   | 15.4 Gm.   | 67.8 Gm.   | 50.4 Gm.   |
| Class 2 | Ex # 53    | Ex # 54    | Ex # 55    | Ex # 57    |
|         | 157.0 Gm.  | 171.0 Gm.  | 185.0 Gm.  | 216.0 Gm.  |
| Class 3 | Ex # 58    | Ex # 58    | Ex # 58    | Ex # 58    |
|         | 0 Gm.      | 0 Gm.      | 0 Gm.      | 0 Gm.      |
| Class 4 | Ex # 62    | Ex # 62    | Ex # 62    | Ex # 62    |
|         | 0 Gm.      | 0 Gm.      | 0 Gm.      | 0 Gm.      |
| Class 5 | Ex # 63    | Ex # 63    | Ex # 63    | Ex # 63    |
|         | 0 Gm.      | 110.0 Gm.  | 1,100 Gm.  | 11.0 Gm.   |
| Class 6 | Ex # 64    | Ex # 64    | Ex # 64    | Ex # 64    |
|         | 0 Gm.      | 0 Gm.      | 0 Gm.      | 0 Gm.      |
| Water   | 250 Gm.    | 600 Gm.    | 3,000 Gm.  | 150 Gm.    |

Catalyst These examples used 0.05% by weight of batch of azobisisobutylnitrile

|         | Example 74 | Example 75 | Example 76 | Example 77 |
|---------|------------|------------|------------|------------|
| Class 1 | Ex # 22    | Ex # 23    | Ex # 24    | Ex # 25    |
|         | 4,200 Gm.  | 3,860 Gm.  | 12,747 Gm. | 1,714 Gm.  |
| Class 2 | Ex # 53    | Ex # 55    | Ex # 56    | Ex # 57    |
|         | 0 Gm.      | 157.0 Gm.  | 171.0 Gm.  | 185.0 Gm.  |
| Class 3 | Ex # 58    | Ex # 58    | Ex # 58    | Ex # 59    |
|         | 0 Gm.      | 0 Gm.      | 193.0 Gm.  | 207.0 Gm.  |
| Class 4 | Ex #62     | Ex #62     | Ex #62     | Ex # 62    |
|         | 0 Gm.      | 0 Gm.      | 0 Gm.      | 72.0 Gm.   |
| Class 5 | Ex # 63    | Ex # 63    | Ex # 63    | Ex # 63    |
|         | 0 Gm.      | 0 Gm.      | 0 Gm.      | 0 Gm.      |
| Class 6 | Ex # 64    | Ex # 64    | Ex # 64    | Ex # 64    |
|         | 0 Gm.      | 0 Gm.      | 0 Gm.      | 0 Gm.      |
| Water   | 4,200 Gm.  | 5,000 Gm.  | 15,000 Gm. | 2,500 Gm.  |

Catalyst These examples used 0.05% by weight of batch of azobisisobutylnitrile

|         | Example 78 | Example 79 | Example 80 | Example 81 |
|---------|------------|------------|------------|------------|
| Class 1 | Ex # 26    | Ex # 27    | Ex # 28    | Ex # 29    |
|         | 1,355 Gm.  | 15,415 Gm. | 6,789 Gm.  | 5,043 Gm.  |
| Class 2 | Ex #53     | Ex # 54    | Ex # 55    | Ex # 56    |
|         | 216.0 Gm.  | 1,570 Gm.  | 1,710 Gm.  | 1,850 Gm.  |
| Class 3 | Ex # 58    | Ex # 59    | Ex # 60    | Ex # 61    |
|         | 215.0 Gm.  | 231.0 Gm.  | 193.0 Gm.  | 207.0 Gm.  |
| Class 4 | Ex # 62    | Ex # 62    | Ex # 62    | Ex # 62    |
|         | 0 Gm.      | 0 Gm.      | 0 Gm.      | 0 Gm.      |
| Class 5 | Ex # 63    | Ex # 63    | Ex # 63    | Ex # 63    |
|         | 110.0 Gm.  | 110.0 Gm.  | 110.0 Gm.  | 1,100 Gm.  |
| Class 6 | Ex # 64    | Ex # 64    | Ex # 64    | Ex # 64    |
|         | 0 Gm.      | 0 Gm.      | 0 Gm.      | 158.0 Gm.  |
| Water   | 2,000 Gm.  | 22,000 Gm. | 10,000 Gm. | 10,000 Gm. |

Catalyst These examples used 0.05% by weight of batch of t-butyl-hydroperoxide (Lucidol TBHP-70-X)

|  | Example 82 | Example 83 | Example 84 | Example 85 |
|---|---|---|---|---|
| Class 1 | Ex # 30 | Ex # 31 | Ex # 32 | Ex # 31 |
|  | 4,200 Gm. | 3,860 Gm. | 12,747 Gm. | 1,714 Gm. |
| Class 2 | Ex # 55 | Ex # 54 | Ex # 53 | Ex # 57 |
|  | 0 Gm. | 0 Gm. | 0 Gm. | 0 Gm. |
| Class 3 | Ex # 58 | Ex # 58 | Ex # 58 | Ex # 58 |
|  | 0 Gm. | 0 Gm. | 0 Gm. | 0 Gm. |
| Class 4 | Ex # 62 | Ex # 62 | Ex # 62 | Ex # 62 |
|  | 0 Gm. | 0 Gm. | 0 Gm. | 0 Gm. |
| Class 5 | Ex # 63 | Ex # 63 | Ex # 63 | Ex # 63 |
|  | 4,200 Gm. | 110.0 Gm. | 30,000 Gm. | 100.0 Gm. |
| Class 6 | Ex # 64 | Ex # 64 | Ex # 64 | Ex # 64 |
|  | 0 Gm. | 0 Gm. | 0 Gm. | 0 Gm. |
| Water | 10,000 Gm. | 5,000 Gm. | 55,000 Gm. | 1,000 Gm. |

Catalyst These examples used 0.07% by weight of batch of t-butyl-hydroperoxide (Lucidol TBHP-70-X)

|  | Example 86 | Example 87 | Example 88 | Example 89 |
|---|---|---|---|---|
| Class 1 | Ex # 31 | Ex # 22 | Ex # 23 | Ex # 24 |
|  | 135.5 Gm. | 154.1 Gm. | 67.9 Gm. | 50.4 Gm. |
| Class 2 | Ex # 53 | Ex # 53 | Ex # 53 | Ex # 53 |
|  | 1,570 Gm. | 0 Gm. | 0 Gm. | 0 Gm. |
| Class 3 | Ex # 68 | Ex # 69 | Ex # 60 | Ex # 61 |
|  | 0 Gm. | 1,930 Gm. | 0 Gm. | 0 Gm. |
| Class 4 | Ex # 62 | Ex # 62 | Ex # 62 | Ex # 62 |
|  | 0 Gm. | 0 Gm. | 720 Gm. | 0 Gm. |
| Class 5 | Ex # 63 | Ex # 63 | Ex # 63 | Ex # 63 |
|  | 0 Gm. | 0 Gm. | 0 Gm. | 1,100 Gm. |
| Class 6 | Ex # 64 | Ex # 64 | Ex # 64 | Ex # 64 |
|  | 0 Gm. | 0 Gm. | 0 Gm. | 0 Gm. |
| Water | 1,000 Gm. | 1,000 Gm. | 1,000 Gm. | 2,000 Gm. |

Catalyst These examples used 0.07% by weight of batch of t-butyl perbenzoate

|  | Example 90 | Example 91 | Example 92 | Example 93 |
|---|---|---|---|---|
| Class 1 | Ex # 32 | Ex # 31 | Ex # 30 | Ex # 29 |
|  | 420.0 Gm. | 386.0 Gm. | 1,274 Gm. | 171.4 Gm. |
| Class 2 | Ex # 56 | Ex # 55 | Ex # 56 | Ex # 57 |
|  | 216.0 Gm. | 2,160 Gm. | 2.16 Gm. | 2,160 Gm. |
| Class 3 | Ex # 58 | Ex # 59 | Ex # 60 | Ex # 61 |
|  | 0 Gm. | 0 Gm. | 0 Gm. | 0 Gm. |
| Class 4 | Ex # 62 | Ex # 62 | Ex # 62 | Ex # 62 |
|  | 0 Gm. | 0 Gm. | 0 Gm. | 0 Gm. |
| Class 5 | Ex # 63 | Ex # 63 | Ex # 63 | Ex # 63 |
|  | 110.0 Gm. | 1,100 Gm. | 11.0 Gm. | 0 Gm. |
| Class 6 | Ex # 64 | Ex # 64 | Ex # 64 | Ex # 64 |
|  | 0 Gm. | 0 Gm. | 0 Gm. | 0 Gm. |
| Water | 500 Gm. | 1,000 Gm. | 5,000 Gm. | 10,000 Gm. |

Catalyst These examples used 0.05% by weight of batch of t-butyl perbenzoate

Applications Examples

The polymers of the present invention are very substantive conditioners to the hair and are surprisingly mild to the skin and eyes. Eye irritation is a major concern in the formulation of personal care products, particularly when working with quats. Primary eye irritation was tested using the protocol outlined in FHSLA 16 CFR 1500.42. The products were tested at 25% actives. The results were as follows.

What is claimed is:

1. A polymer conforming to the following generic structure;

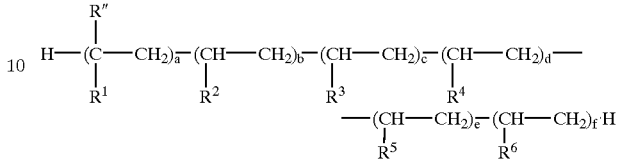

wherein;

R″ is selected from the group consisting of CH3 and H;

a is an integer from 1 to 100;

b, c, d, e and f are integers ranging from 0 to 100, with the proviso that a+b+c+d+e+f equal at least 2;

$R^1$ is —$CH_2$—O—$(CH_2CH_2O)_s$—$(CH_2CH(CH_3)O)_t$—$(CH_2CH_2O)_u$P(O)—$(OH)_2$ s, t and u are independently integers ranging from 0 to 20;

$R^2$ is —C(O)—O $\overline{M}^+$

M is selected from H, Na, K, Li, and NH 4;

$R^3$ is

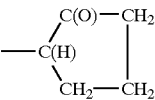

$R^4$ is

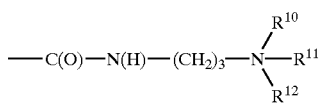

$R^{10}$, $R^{11}$ and $R^{12}$ are selected from H, methyl and ethyl;

$R^5$ is —C(O)—$NH_2$ $R^5$ is —C(O)—N(H)—$(CH_2)_q$—$SO_3^-M^+$ q is an integer ranging from 1 to 5.

2. A polymer of claim 1 wherein c, d, e, and f are all zero and a and b are independently integers ranging from 1 to 100, with the proviso that a+b equal at least 2.

3. A polymer of claim 1 wherein b, d, e and f are all zero and a and c are independently integers ranging from 1 to 100, with the proviso that a+c equal at least 2.

4. A polymer of claim 1 wherein b, c, e and f are all zero and a and d are independently integers ranging from 1 to 100, with the proviso that a+d equal at least 2.

5. A polymer of claim 1 wherein b, c, d and f are all zero and a and e are independently integers ranging from 1 to 100, with the proviso that a+e equal at least 2.

6. a polymer of claim 1 wherein b, c, d and e are all zero and a and f are independently integers ranging from 1 to 100, with the proviso that a+f equal at least 2.

* * * * *